(12) United States Patent (10) Patent No.: US 7,978,916 B2
Klingensmith et al. (45) Date of Patent: *Jul. 12, 2011

(54) SYSTEM AND METHOD FOR IDENTIFYING A VASCULAR BORDER

(75) Inventors: Jon D. Klingensmith, Shaker Heights, OH (US); D. Geoffrey Vince, Avon Lake, OH (US); Anuja Nair, Cleveland Heights, OH (US); Barry D. Kuban, Avon Lake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 301 days.

This patent is subject to a terminal disclaimer.

(21) Appl. No.: 12/102,661

(22) Filed: Apr. 14, 2008

(65) Prior Publication Data

US 2008/0287795 A1 Nov. 20, 2008

Related U.S. Application Data

(63) Continuation of application No. 10/649,473, filed on Aug. 26, 2003, now Pat. No. 7,359,554.

(60) Provisional application No. 60/406,148, filed on Aug. 26, 2002, provisional application No. 60/406,183, filed on Aug. 26, 2002, provisional application No. 60/406,184, filed on Aug. 26, 2002, provisional application No. 60/406,185, filed on Aug. 26, 2002, provisional application No. 60/406,234, filed on Aug. 26, 2002, provisional application No. 60/406,254, filed on Aug. 26, 2002.

(51) Int. Cl.
*G06K 9/48* (2006.01)
*G06K 9/00* (2006.01)
*A61B 6/00* (2006.01)
*A61F 11/00* (2006.01)

(52) U.S. Cl. ......... 382/199; 382/131; 600/467; 606/108
(58) Field of Classification Search .................. 382/199, 382/128–134; 600/443, 463, 462, 467, 437, 600/468, 459, 439, 485, 483, 454, 407, 466; 606/108, 191; 128/916; 604/529
See application file for complete search history.

(56) References Cited

U.S. PATENT DOCUMENTS 4,228,804 A 10/1980 Holasek
(Continued)

FOREIGN PATENT DOCUMENTS

EP 0 663 548 B1 1/2002

OTHER PUBLICATIONS

Sebbahi, A., Herment, A., De Cesare, A., Mousseaux, E., "Multimodality Cardiovascular Image Segmentation Using a Deformable Contour Model", Computerized Medical Imaging and Graphics, 1997, pp. 79-89, vol. 21. No. 2, Pergamon Press. New York, U.S.A.

(Continued)

*Primary Examiner* — Kanji Patel
(74) *Attorney, Agent, or Firm* — Haynes and Boone LLP (57) ABSTRACT

A system and method is provided for using a first vascular image, or more particularly a plurality of control points located thereon, to identify a border on a second vascular image. Embodiments of the present invention operate in accordance with an intra-vascular ultrasound (IVUS) device and a computing device electrically connected thereto. Specifically, in one embodiment of the present invention, an IVUS console is electrically connected to a computing device and adapted to acquire IVUS data. The IVUS data (or multiple sets thereof) is then provided to (or acquired by) the computing device. In one embodiment of the present invention, the computing device includes a plurality of applications operating thereon—i.e., a border-detection application, an extrapolation application, and an active-contour application.

These applications are used to (i) identify a border and control points on a first IVUS image (i.e., any IVUS image), (ii) extrapolate the control points to a second IVUS image (i.e., another IVUS image), (iii) identify a border on the second IVUS image, and (iv) adjust the border on the second IVUS image in accordance with at least one factor. In one embodiment of the present invention, the at least one factor is selected from a group consisting of gradient factor, continuity factor, and curvature factor.

22 Claims, 3 Drawing Sheets

U.S. PATENT DOCUMENTS

| | | | |
|---|---|---|---|
| 4,511,984 | A | 4/1985 | Sumino |
| 4,561,019 | A | 12/1985 | Lizzi |
| 4,575,799 | A | 3/1986 | Miwa |
| 4,858,124 | A | 8/1989 | Lizzi |
| 5,235,984 | A | 8/1993 | D'Sa |
| 5,363,850 | A | 11/1994 | Soni |
| 5,417,215 | A | 5/1995 | Evans |
| 5,445,155 | A | 8/1995 | Sieben |
| 5,559,901 | A | 9/1996 | Lobregt |
| 5,724,972 | A | 3/1998 | Petrofsky |
| 5,876,343 | A | 3/1999 | Teo |
| 5,885,218 | A | 3/1999 | Teo |
| 5,938,607 | A | 8/1999 | Jago |
| 5,957,138 | A | 9/1999 | Lin |
| 6,050,946 | A | 4/2000 | Teo |
| 6,095,976 | A | 8/2000 | Nachtomy |
| 6,106,460 | A | 8/2000 | Panescu |
| 6,106,465 | A | 8/2000 | Napolitano |
| 6,120,445 | A | 9/2000 | Grunwald |
| 6,152,878 | A | 11/2000 | Nachtomy |
| 6,200,268 | B1 | 3/2001 | Vines et al. |
| 6,217,517 | B1 | 4/2001 | Grunwald |
| 6,238,342 | B1 | 5/2001 | Feleppa |
| 6,254,541 | B1 | 7/2001 | Teo |
| 6,287,259 | B1 | 9/2001 | Grunwald |
| 6,306,089 | B1 | 10/2001 | Coleman |
| 6,335,980 | B1 | 1/2002 | Armato |
| 6,381,350 | B1 | 4/2002 | Klingensmith et al. |
| 6,454,715 | B2 | 9/2002 | Teo |
| 6,514,202 | B2 | 2/2003 | Grunwald |
| 6,544,187 | B2 | 4/2003 | Seward |
| 6,561,980 | B1 | 5/2003 | Cheng |
| 6,785,409 | B1 | 8/2004 | Suri |
| 7,359,554 | B2 * | 4/2008 | Klingensmith et al. ...... 382/199 |
| 2001/0014774 | A1 | 8/2001 | Grunwald |
| 2003/0028118 | A1 | 2/2003 | Dupree |
| 2003/0092993 | A1 | 5/2003 | Grunwald |

OTHER PUBLICATIONS

Tsutsui, H., Ziada, K., Schoenhagen, P., Iyisoy, A., Magyar, W., Crowe, T., Klingensmith, J., Vince, D.. Rincon, G., Hobbs, R., Yamagishi, M., Nissen, S., Tuzcu, E., "Lumen Loss in Transplant Coronary Artery Disease Is a Biphasic Process Involving Early Intimal Thickening and Late Constrictive Remodeling: Results from a 5-Year Serial Intravascular Ultrasound Study", Circulation, 2001, pp. 653-657, vol. 104, No. 6, American Heart Association, Dallas. U.S.A.

Von Birgelen, C., Di Mario. C., Li, W., Schuurbiers, J., Slager, C.. De Feyter, P., Roelandt, J., Serruys, P., "Morphometric Analysis in Three-Dimensional Intracoronary Ultrasound: An In Vitro and In Vivo Study Performed with a Novel System for the Contour Detection of Lumen and Plaque", American Heart Journal, 1996, pp. 516-527. vol. 132. No. 3, Elsevier, St. Louis, U.S.A.

Von Birgelen, C., De Vrey, E., Mintz, G., Nicosia, A., Bruining, N., Li, W,. . Slager, C., Roelandt, J., Serruys, P., De Feyter, P., "ECG-Gated Three-Dimensional Intravascular Ultrasound: Feasibility and Reproducibility of the Automated Analysis of Coronary Lumen and Atherosclerotic Plaque Dimensions in Humans", Circulation, 1997. pp. 2944-2952, vol. 96. No. 9, American Heart Association, Dallas. U.S.A.

Nair, A., Kuban, B., Obuchowski, N., and Vince, D., "Assessing Spectral Algorithms to Predict Atherosclerotic Plaque Composition With Normalized and Raw Intravascular Ultrasound Data", Ultrasound in Medicine and Biology. 2001. pp. 1319-1331. vol. 27. No. 10. Bsevier, U.S.A.

Nair, A., Kuban, B., Tuzcu, E., Schoenhagen, P., Nissen, S., and Vince. D., "Coronary Plaque Classification With Intravascular Ultrasound Radiofrequency Data Analysis", Circulation, 2002, pp. 2200-2206; 106, American Heart Association, U.S.A.

Klingensmith, J. and Vince, p., "B-Spline Methods for interactive Segmentation and Modeling of Lumen and Vessel Surfaces in Three-Dimensional Intravascular Ultrasound," Computerized Medical Imaging and Graphics 26, 2002, pp. 429-438, Elsevier Science Ltd.. U.S.A.

Bruining, N., Von Birgelen, C., De Feyter. P., Ligthart. J., Serruys, P., Roelandt, J., "Dynamic Imaging of Coronary Stent Structures: An ECG-Gated Three-Dimensional Intracoronary Ultrasound Study in Humans", Ultrasound in Medicine and Biology. 1998, pp. 631-637, vol. 24, No. 5, Elsevier, New York, U.S.A.

Chen. C.. Lu, H., Hsiao, A., "A Dual-Snake Model of High Penetrability for Ultrasound Image Boundary Extraction", Ultrasound in Medicine and Biology, 2001, pp. 1651-1665, vol. 27. No. 12, Elsevier, New York, U.S.A.

Ko, C., Mao. C., Sun, Y., Chang, S., "A Fully Automated Identification of Coronary Borders from the Tree Structure of Coronary Angiograms", International Journal of Bio-Medical Computing, 1995, pp. 193-208, vol. 39, No. 2. Elsevier, Barking, England.

Kovalski, G., Beyar, R., Shofti, R., Azharl H., "Three-Dimensional Automatic Quantitative Analysis of Intravascular Ultrasound Images", Ultrasound in Medicine and Biology, 2000, pp. 527-537, vol. 26, No. 4, Elsevier, New York, U.S.A.

Iwase, M., Kondo, T., Hasegawa, K,, Kimura. M., Matsuyama. H.. Watanabe. Y.. Hishida. H., "Three-Dimensional Echocardiography by Semi-Automatic Border Detection In Assessment of Left Ventricular vol. and Ejection Fraction: Comparison with Magnetic Resonance Imaging", Journal of Cardiology, 1997, pp. 97-105, vol. 30, No. 2, Japanese College of Cardiology. Tokyo. Japan.

Klingensmith, J., Vince, D., Kuban, B., Shekhar, R., Tuzcu, E.. Nissen, S., Cornhill, J., "Assessment of Coronary Compensatory Enlargement by Three-Dimensional Intravascular Ultrasound", International Journal of Cardiac Imaging. 2000. pp. 87-96, vol. 16, No. 2. Nijhoff, Boston. U.S.A.

Klingensmith, J., Shekhar, R., Vince. D., "Evaluation of Three-Dimensional Segmentation Algorithms for the Identification of Luminal and Medial-Adventitial Borders in Intravascular Ultrasound Images", IEEE Transactions on • Medical Imaging, 2000, pp. 996-1011, vol. 19, No. 10, Institute of Electrical and Electronics Engineers, New York, U.S.A.

Lobregt, S., Viergever, M., "A Discrete Dynamic Contour Model", IEEE Transactions on Medical Imaging. 1995. pp. 12-24, vol. 14, No. 1. Institute of Electrical and Electronics Engineers. New York, U.S.A.

* cited by examiner

SYSTEM AND METHOD FOR IDENTIFYING A VASCULAR BORDER

CROSS-REFERENCE TO RELATED APPLICATIONS

This is a continuation of U.S. patent application Ser. No. 10/649,473, filed on Aug. 26, 2003, which claims the benefit pursuant to 35 U.S.C. §119(e) of U.S. Provisional Patent Application Ser. Nos. 60/406,148, 60/406,183, 60/406,184, 60/406,185, 60/406,234, and 60/406,254, all of which were filed on Aug. 26, 2002, and all are explicitly incorporated herein by reference in their entirety including an references contained therein.

BACKGROUND OF THE INVENTION

1. Field of the Invention

The present invention relates to vascular borders, or more particularly, to a system and method of using a first vascular image (or control points located therein) to identify a border on a second vascular image.

2. Description of Related Art

The present invention relates to medical imaging arts. It finds particular application to a system and method of, identifying a border in an intra-vascular ultrasound (IVUS) image. It should be appreciated that while the present invention is described in terms of identifying a luminal and medial-adventitial border on an IVUS image, the present invention is not so limited. Thus, for example, identifying any border (or boundary) in any vascular image is within the spirit and scope of the present invention.

Ultrasonic imaging of portions of a patient's body provides a useful tool in various areas of medical practice for determining the best type and course of treatment. Imaging of the coronary vessels of a patient by ultrasonic techniques can provide physicians with valuable information. For example, the image data may show the extent of a stenosis in a patient, reveal progression of disease, help determine whether procedures such as angioplasty or atherectomy are indicated or whether more invasive procedures may be warranted.

In a typical ultrasound imaging system, an ultrasonic transducer is attached to the end of a catheter that is carefully maneuvered through a patient's body to a point of interest such as within a blood vessel. The transducer may be a single-element crystal or probe that is mechanically scanned or rotated back and forth to cover a sector over a selected angular range. Acoustic signals are then transmitted and echoes (or backscatter) from these acoustic signals are received. The backscatter data can be used to identify the type or density of a scanned tissue. As the probe is swept through the sector, many acoustic lines are processed building up a sector-shaped image of the patient. After the data is collected, an image of the blood vessel (i.e., an IVUS image) is reconstructed using well-known techniques. This image is then visually analyzed by a cardiologist to assess the vessel components and plaque content.

A typical analysis includes determining the size of the lumen and amount of plaque in the vessel. This is performed by generating an image of the vessel (e.g., an IVUS image) and manually drawing contoured boundaries on the image where the clinician believes the luminal and the medial-adventitial borders are located. This is a very time consuming process. Furthermore, this process is made more difficult when multiple images are being analyzed (e.g., to recreate a 3D vascular image, etc.) or the images are of poor quality (e.g., making the boundaries more difficult to see). Thus, it would advantageous to have a system and method of identifying a border on a vascular image that overcomes at least one of these drawbacks.

SUMMARY OF THE INVENTION

The present invention provides a system and method of using a first vascular image, or more particularly a plurality of control points located thereon, to identify a border on a second vascular image. Embodiments of the present invention operate in accordance with an intra-vascular ultrasound (IVUS) device and a computing device electrically connected thereto. Specifically, in one embodiment of the present invention, an IVUS console is electrically connected to a computing device and a transducer via a catheter. The transducer is inserted into a blood vessel of a patient and used to gather IVUS data (i.e., blood-vessel data, or data that can be used to identify the shape of a blood vessel, its density, its composition, etc.). The IVUS data is then provided to (or acquired by) the IVUS console, where it is used to produce an IVUS image of the vessel.

The IVUS data (or multiple sets thereof) is then provided to (or acquired by) the computing device. In one embodiment of the present invention, the computing device includes a plurality of applications operating thereon—i.e., a border-detection application, an extrapolation application, and an active-contour application. These applications are used to (i) identify a border and control points on a first IVUS image (i.e., any IVUS image), (ii) extrapolate the control points to a second IVUS image (i.e., another IVUS image), (iii) identify a border on the second IVUS image, and (iv) adjust the border on the second IVUS image in accordance with at least one factor.

Specifically, the border-detection application is adapted to identify a border on a vascular image (e.g., an IVUS image). In one embodiment of the present invention, this is accomplished by analyzing the IVUS image, or IVUS data that corresponds to the IVUS image, to determine certain gradients located therein. This is because borders of vascular objects can be identified by a change in pixel color (e.g., light-to-dark, dark-to-light, shade1-to-shade2, etc). Once the border is identified, the border-detection application is used to identify at least one control point (i.e., a starting-control point) on the identified border. The extrapolation application is then used to identify at least one control point (i.e., an additional control point) on at least one other IVUS image. In a preferred embodiment of the present invention, this is done by extrapolating the previously identified control point (i.e., the starting-control point) to at least one other IVUS image. Once the control point(s) is extrapolated, the extrapolating application is adapted to identify (or approximate) a border that passes through the extrapolated point(s).

The active-contour application is then used to adjust the approximated border (i.e., the border passing through the extrapolated point(s)) to more closely match the actual border of the vascular object. In doing so, the active-contour application may consider, or take into account at least (i) image gradients (i.e., gradient factor), (ii) the proximity of the border to each extrapolated point (i.e., continuity or control-point factor), and/or (iii) border curvature or smoothness (i.e., curvature or boundary factor). Specifically, the gradient factor can be used to adjust the border if the neighboring pixels (as opposed to the pixels of the border) include border characteristics (e.g., a dark-to-light transition, etc.). In other words, if the neighboring pixels include border-like characteristics (or at least more so than the pixels forming the border), then the border is adjusted. The continuity factor and the curvature factor can be used to ensure that the border passes through each extrapolated point and does not include any sharp transitions (e.g., corners, etc.), respectively. In one embodiment of the present invention, the active-contour application is further adapted to adjust related borders on adjacent images if the boarder is manually adjusted.

A more complete understanding of the system and method of identifying a border on an IVUS image will be afforded to those skilled in the art, as well as a realization of additional advantages and objects thereof, by a consideration of the following detailed description of the preferred embodiment. Reference will be made to the appended sheets of drawings which will first be described briefly.

DETAILED DESCRIPTION OF THE PREFERRED EMBODIMENT

The present invention provides a system and method of using a first vascular image, or more particularly a plurality of control points located thereon, to identify a border on a second vascular image. In the detailed description that follows, like element numerals are used to describe like elements illustrated in one or more figures.

Figure 1:
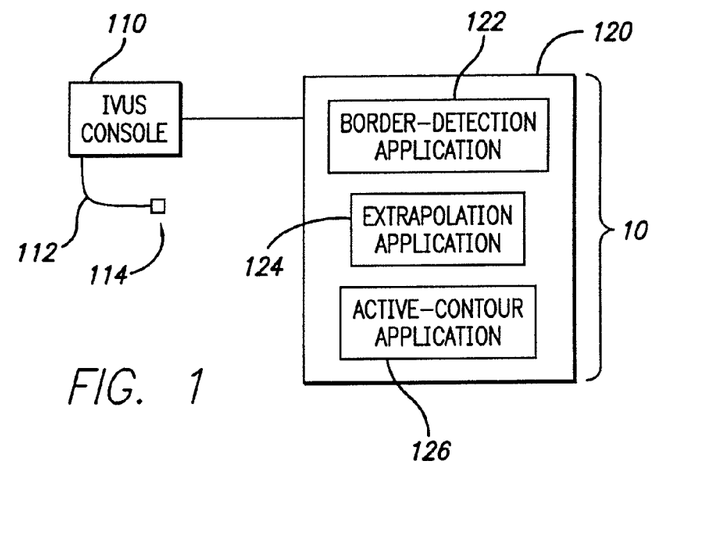
FIG. 1 illustrates a vascular-border-identification system in accordance with one embodiment of the present invention.

Embodiments of the present invention operate in accordance with an intra-vascular ultrasound (IVUS) device and a computing device electrically connected thereto. FIG. 1 illustrates a vascular-border-identification system 10 in accordance with one embodiment of the present invention. Specifically, an IVUS console 110 is electrically connected to a computing device 120 and a transducer 114 via a catheter 112. The transducer 114 is inserted into a blood vessel of a patient (not shown) and used to gather IVUS data (i.e., blood-vessel data, or data that can be used to identify the shape of a blood vessel, its density, its composition, etc.). The IVUS data is then provided to (or acquired by) the IVUS console 110, where it is used to produce an IVUS image of the vessel.

More particularly, IVUS data is typically gathered in segments, either through a rotating transducer or an array of circumferentially positioned transducers, where each segment represents an angular portion of an IVUS image. Thus, it takes a plurality of segments (or a set of IVUS data) to image an entire cross-section of a vascular object. Furthermore, multiple sets of IVUS data are typically gathered from multiple locations within a vascular object (e.g., by moving the transducer linearly through the vessel). These multiple sets of data can then be used to create a plurality of two-dimensional (2D) images or one three-dimensional (3D) image. It should be appreciated that the present invention is not limited to the use of an IVUS device (or the acquisition of IVUS data), and may further include using thermographic devices, optical devices (e.g., an optical coherence tomography (OCT) console), MRI devices, or any vascular imaging devices generally known to those skilled in the art. It should further be appreciated that the computing device depicted in FIG. 1 includes, but its not limited to, personal computers or any other data-processing devices (general purpose or application specific) that are generally known to those skilled in the art.

The IVUS data (or multiple sets thereof) is then provided to (or acquired by) the computing device 120. In one embodiment of the present invention, the computing device 120 includes a plurality of applications operating thereon—i.e., a border-detection application 122, an extrapolation application 124, and an active-contour application 126. These applications are used to (i) identify a border and control points on a first IVUS image (i.e., any IVUS image), (ii) extrapolate the control points to a second IVUS image (i.e., another IVUS image), (iii) identify a border on the second IVUS image, and (iv) adjust the border on the second IVUS image. It should be appreciated that the number and/or location of the applications depicted in FIG. 1 are not intended to limit the present invention, but are merely provided to illustrate the environment in which the present invention operates. Thus, for example, using a single application to perform the application functions, as discussed herein, or remotely locating at least one of the applications (in whole or in part) is within the spirit and scope of the present invention. It should further be appreciated that, while the present invention is discussed in terms of singularities (e.g., identifying a border on one IVUS image, extrapolating control points to another IVUS image, etc.), the present invention is not so limited. In fact, the present invention is particularly useful if it is used on a plurality of IVUS images (e.g., identifying borders on every fifth IVUS image, extrapolating control points from the fifth IVUS image to the next four IVUS images, etc.). It should also be appreciated that the terms "first" and "second," as those terms are used herein, are used broadly to identify any two IVUS images. Thus, the phrase "second IVUS image" may be used to identify an IVUS image distinct from a first IVUS image (as opposed to the second IVUS image in a series of IVUS images).

Vascular objects include several identifiable borders. For example, the luminal border demarcates the blood-intima interface and the medial-adventitial border demarcates the external elastic membrane (the boundary between the media and adventitia). By identifying these borders, the plaque-media complex, which is located there between, can be analyzed and/or calculated. It should be appreciated that the present invention is not limited to the identification of any particular border, and includes all vascular boundaries generally known to those skilled in the art.

Referring back to FIG. 1, the border-detection application 122 is adapted to identify a border on a vascular image (e.g., an IVUS image). In one embodiment of the present invention, this is performed by analyzing the IVUS image, or IVUS data that corresponds the IVUS image, to determine certain gradients located therein. This is because borders of vascular objects can be identified by a change in pixel color (e.g., light-to-dark, dark-to-light, shade1-to-shade2, etc).

Figure 2:
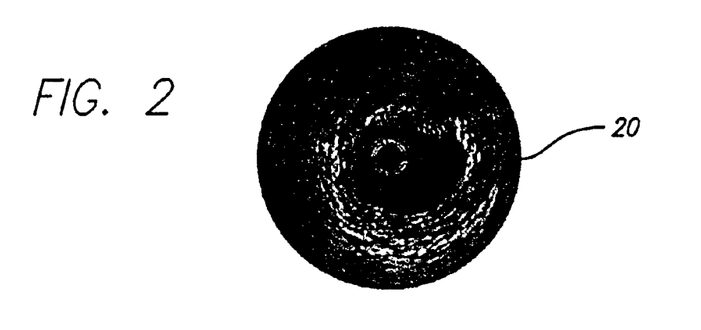
FIG. 2 illustrates and exemplary intra-vascular ultrasound (IVUS) image.
Figure 3:
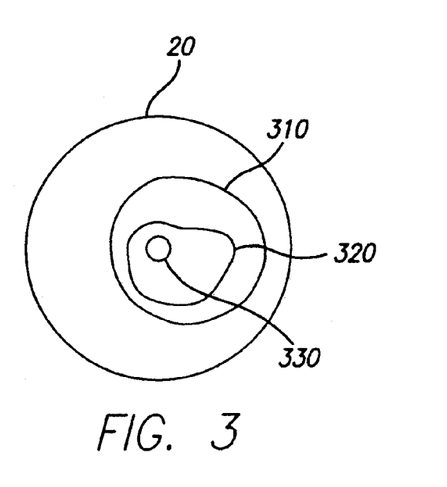
FIG. 3 illustrates a plurality of borders that can be identified in an IVUS image.

For example, FIG. 2 illustrates an exemplary IVUS image 20 of a vascular object. Starting from the center and working outward, the catheter can be identified by the first light-todark transition (or gradient). The catheter border is further identified in FIG. 3 (i.e., 330). Referring back to FIG. 2, and continuing outward, the next dark-to-light transition (or gradient) identifies the luminal border (i.e., see FIG. 3, 320). The medial-adventitial border can then be identified by going outward from the luminal border until the next dark-to-light transition (or gradient) is found (see FIG. 3, 310). It should be appreciated that because the IVUS image is constructed using gray-scales, it may be necessary to utilize an algorithm and/or at least one threshold value to identify precisely where the image changes from light to dark (or vice versa). However, it should further be appreciated that the present invention is not limited to any particular algorithm for identifying the aforementioned transitions, and includes all algorithms (and/or threshold values) generally known to those skilled in the art.

Figure 4:
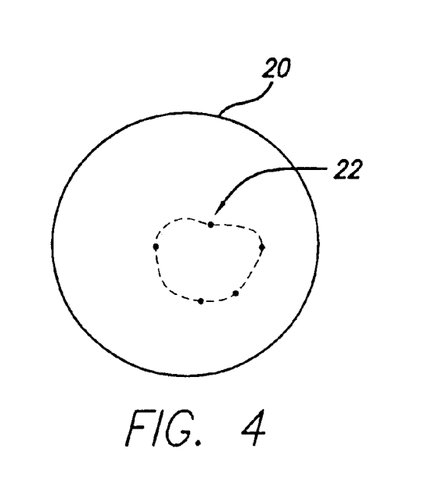
FIG. 4 illustrates a plurality of control points on one of the borders depicted in FIG. 3.

Once the border is identified, the border-detection algorithm is further adapted to identify at least one control point on the border. For example, with reference to FIGS. 3 and 4, the border-detection algorithm can be used to identify a plurality of control points 22 on the luminal border 320. It should be appreciated that the location and number of control points depicted in FIG. 4 are not intended to limit the present invention, and are merely provided to illustrate the environment in which the present invention may operate. In an alternate embodiment, the border-detection application 122 is adapted to identify a border using user-identified control points. Such an embodiment is discussed in detail in U.S. Pat. No. 6,381,350, which issued Apr. 30, 2002, and is incorporated herein, in its entirety, by reference.

Figure 5:
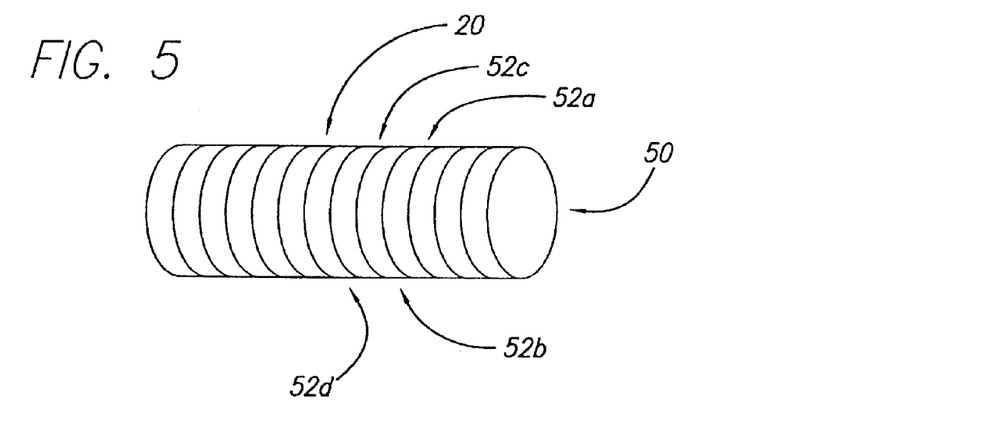
FIG. 5 illustrates how a plurality of 2D vascular images can be used to generate a 3D vascular image.

Referring back to FIG. 1, once the border and control point(s) are identified on a first vascular image, the extrapolation application 124 is used to identify at least one control point on at least one other IVUS image. In a preferred embodiment of the present invention, this is done by extrapolating the previously identified control points to at least one other IVUS image. By doing this, multiple 2D images (or at least one 3D image) can be produced. For example, as illustrated in FIG. 5, multiple 2D images (e.g., 20, 52a-52d, etc.) are used to produce a 3D image of a tubular (e.g., vascular) object 50.

Figure 6:
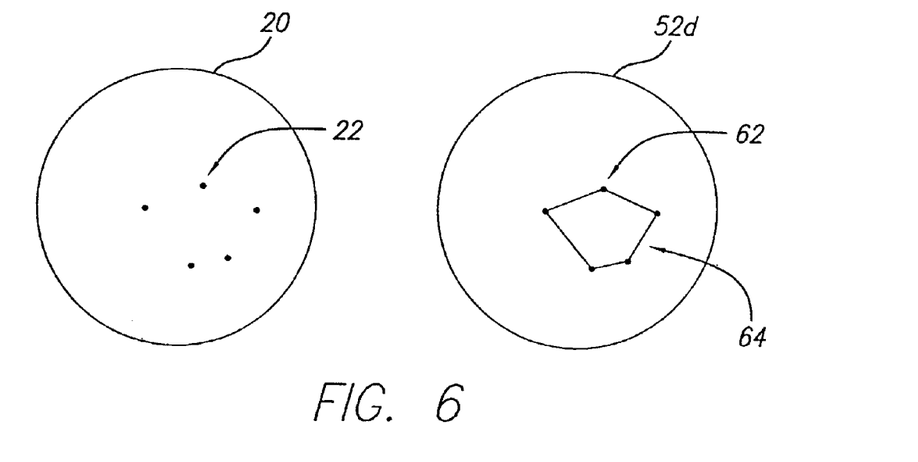
FIG. 6 illustrates how the control points from a first image (e.g., the image depicted in FIG. 4) can be extrapolated onto a second image.

FIG. 6 illustrates how an identified control point can be extrapolated to another IVUS image. Specifically, the control points that were illustrated in FIG. 4 (i.e., 22) are extrapolated (or copied) to another IVUS image (e.g., 52d), thus creating a second set of control points 62. In one embodiment of the present invention, the control points are extrapolated using Cartesian coordinates. It should be appreciated that, while FIG. 6 illustrates control points being extrapolated to an adjacent image, the present invention is not so limited. Thus, extracting control points to additional images (e.g., 52c, 52b, etc.) is within the spirit and scope of the present invention.

Once the control points are extrapolated, the extrapolating application is further adapted to identify (or approximate) a border based on the extrapolated points. For example, as shown in FIG. 6, the extrapolated points 62 may be connected using a plurality of lines 64, where the lines are either straight or curved (not shown). In another embodiment of the present invention, the extrapolating application is adapted to use an algorithm (e.g., a cubic-interpolation algorithm, etc.) to identify line shape.

Referring back to FIG. 1, the active-contour application 126 is then used to adjust the border to more closely match the actual border of the vascular object. In doing so, the active-contour application 126 may consider or take into account at least (i) image gradients (i.e., gradient data), (ii) the proximity of the border to each extrapolated point (i.e., continuity or control-point factor), and/or (iii) border curvature or smoothness (i.e., curvature or boundary factor). Specifically, by considering gradient data (or a gradient factor), the border can be adjusted if the neighboring pixels (as opposed to the pixels of the border) include border characteristics (e.g., a dark-to-light transition, etc.). By considering a continuity or control-point factor, the border can be adjusted so that it passes through each extrapolated point. Furthermore, by considering a curvature or boundary factor, the border can be adjusted to prevent sharp transitions (e.g., corners, etc.). In one embodiment of the present invention, the continuity and curvature factors are also used to connect related borders on adjacent images. It should be appreciated that if multiple factors are being considered, then individual factors may be weighted more heavily than others. This becomes important if the factors produce different results (e.g., the gradient factor suggests adjusting the border away from an extrapolated point, etc.). It should further be appreciated that the active-contour application may also be used to adjust the border identified by the border-detection application. It should also be appreciated that the present invention is not limited to the use of the aforementioned factors for border optimization, and that the use of additional factors (e.g., frequency factor, etc.) to adjust (or optimize) a border is within the spirit and scope of the present invention.

In one embodiment of the present invention, the adjusted borders are configured to be manually manipulated. In other words, at least one point on the border can be selected and manually moved to a new location. The active-contour application is then used (as previously discussed) to reconstruct the border accordingly. In another embodiment of the present invention, the active-contour application is further adapted to adjust related borders in adjacent images. This is done by fitting a geometrical model (e.g., a tensor product B-spline, etc.) over the surface of a plurality of related borders (e.g., as identified on multiple IVUS images). A plurality of points on the geometrical model are then parameterized and formulated into a constrained least-squares system of equations. If a point on the border is manually moved, the active-contour application can utilize these equations to calculate a resulting surface (or mesh of control points). The affected borders (e.g., adjacent borders) can then be adjusted accordingly.

Figure 7:
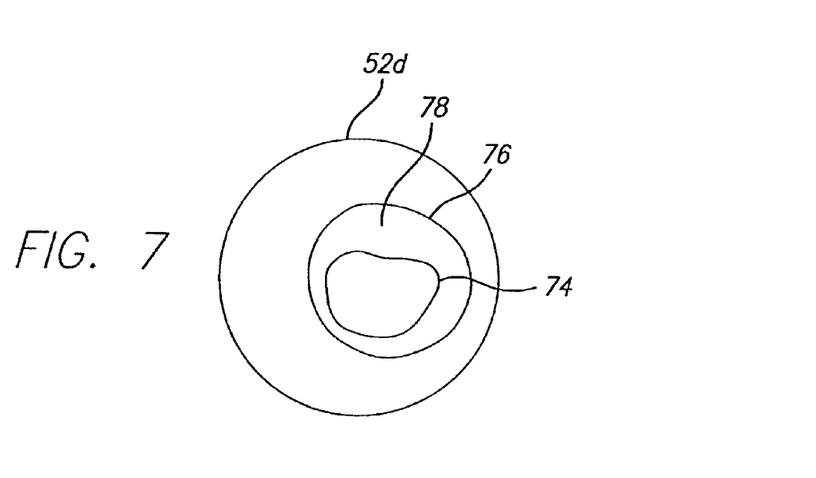
FIG. 7 illustrates a vascular image including a luminal boundary, a medial-adventitial boundary, and a plaque component located therebetween.

Once the border has been sufficiently adjusted, the aforementioned process can be repeated to identify additional borders. In an alternate embodiment of the present invention, multiple borders (e.g., luminal and medial-adventitial borders) are identified concurrently. The multiple border can then be imaged (in either 2D or 3D) and analyzed by either a skilled practitioner or a computer algorithm. For example, as illustrated in FIG. 7, the luminal border 74 and the medial-adventitial border 76 can be used (by either a clinician or an algorithm) to identify the plaque-media complex 78 of a vascular object.

Figure 8:
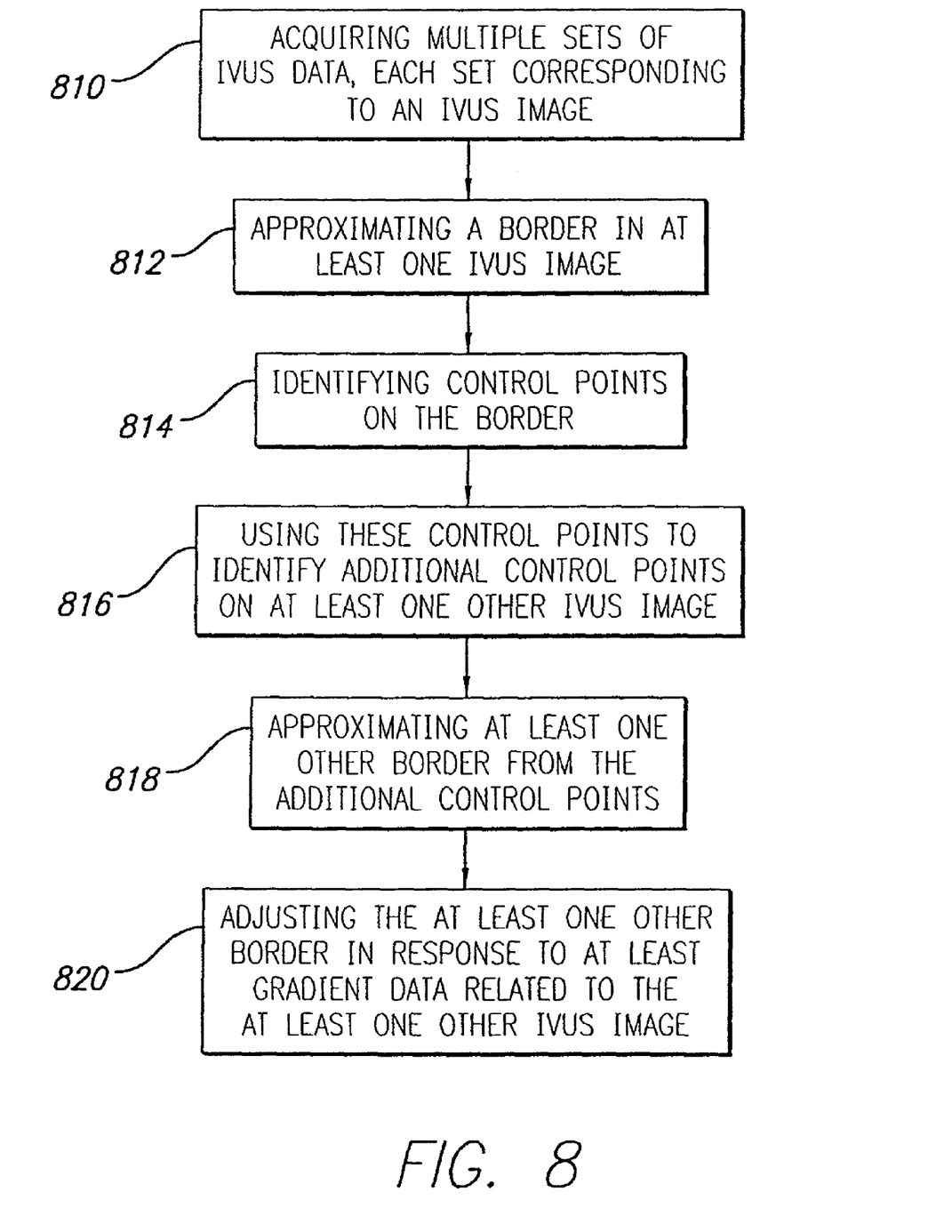
FIG. 8 illustrates a method of identifying a border of a vascular object in accordance with one embodiment of the present invention.

One method of identify a border on a vascular image is illustrated in FIG. 8. Specifically, in step 810, multiple sets of IVUS data are acquired, where each set of IVUS data corresponds to a 2D IVUS image. At step 812, a border is approximated in one IVUS image (e.g., using gradient data, etc.). Control points on the approximated border are then identified at step 814. At step 816, these control points are then used to identify additional control points on additional 2D IVUS images (e.g., via extrapolation, etc.). These additional control points are then used to approximate at least one other border at step 818, which is then adjusted at step 820. In one embodiment, the border is adjusted in accordance with at least gradient data.

Having thus described a preferred embodiment of a system and method of identifying a border on a vascular image, it should be apparent to those skilled in the art that certain advantages of the system have been achieved. It should also be appreciated that various modifications, adaptations, and alternative embodiments thereof may be made within the scope and spirit of the present invention. The invention is further defined by the following claims.

What is claimed is:

1. A method of identifying a border of a vascular object, comprising:
   a computing device adapted to be electrically connected to a data-gathering device to perform the steps of:
   acquiring multiple sets of blood-vessel data, each set corresponding to an image of a vascular object;
   using a set of blood-vessel data to approximate a border on an image of said vascular object;
   identifying at least one control point on said border;
   extrapolating said at least one control point to at least one other set of blood-vessel data, creating at least one other control point on at least one other image;
   using said at least one other control point to approximate at least one other border on said at least one other image; and
   adjusting said at least one other border in accordance with at least a frequency factor.

2. The method of claim 1, wherein said step of acquiring multiple sets of blood-vessel data further comprises acquiring multiple sets of intra-vascular ultrasound (IVUS) data, where each set corresponds to an IVUS image of said vascular object.

3. The method of claim 1, wherein said step of using a set of blood-vessel data to approximate a border further comprises identifying gradients in said image and using said gradients to approximate said border on said image of said vascular object.

4. The method of claim 1, wherein said step of extrapolating said at least one control point further comprises extrapolating said at least one control point to an adjacent set of blood-vessel data, said adjacent set corresponding to another image adjacent to said image.

5. The method of claim 1, wherein said step adjusting said at least one other border further comprises adjusting said at least one other border in accordance with at least a continuity factor, said continuity factor representing an amount of continuity between adjacent control points on said at least one other border.

6. The method of claim 1, wherein said step of adjusting said at least one other border further comprises adjusting said at least one other border in accordance with at least a curvature factor, said curvature factor representing an amount of continuity between adjacent portions of said at least one other border.

7. The method of claim 5, wherein said step of adjusting said at least one other border further comprises adjusting said at least one other border in accordance with at least a curvature factor, said curvature factor representing an amount of continuity between adjacent portions of said at least one other border.

8. The method of claim 4, further comprising automatically adjusting an adjacent border if said border is manually adjusted, said adjacent border being located on said another image.

9. A border-identification system comprising:
   a computing device adapted to be electrically connected to a data-gathering device and to acquire from said data-gathering device multiple sets of blood-vessel data, each set corresponding to an image of a vascular object;
   a border-detection application operating on said computing device and adapted to use at least a portion of said blood-vessel data to produce starting-border data and starting-control-point data, said starting-border data representing at least one border on at least one image of said vascular object and said starting-control-point data representing at least one control point on said at least one border;
   an extrapolation application operating on said computing device and adapted to use said starting-control-point data to produce additional-control-point data and additional-border data, said additional-control-point data representing at least one other control point on at least one other image and said additional-border data representing at least one other border on said at least one other image; and
   an active-contour application operating on said computing device and adapted to adjust said at least one other border in accordance with at least a frequency factor.

10. The border-identification system of claim 9, wherein said data-gathering device comprises an intra-vascular ultrasound (IVUS) console.

11. The border-identification system of claim 9, wherein said border-detection application is further adapted to identify gradients in said at least one image and use said gradients to produce starting-border data.

12. The border-identification system of claim 11, wherein said border-detection application is further adapted to use said starting-border data to produce said starting-control-point data.

13. The border-identification system of claim 9, wherein said extrapolation application is further adapted to produce said additional-border data by using cubic interpolation to connect adjacent ones of said at least one other control point.

14. The border-identification system of claim 9, wherein said active-contour application is further adapted to use gradient data to adjust said at least one other border, said gradient data representing gradients in said at least one other image.

15. The border-identification system of claim 14, wherein said active-contour application is further adapted to consider the continuity of adjacent ones of said at least one other control point in adjusting said at least one other border.

16. The border-identification system of claim 15, wherein said active-contour application is further adapted to consider the curvature of said at least one other border in adjusting said at least one other border.

17. The border-identification system of claim 9, wherein said active-contour application is further adapted to adjust said at least one other border in accordance with at least one factor, said at least one factor being selected from the group consisting of a gradient factor, a continuity factor and a curvature factor.

18. A method of identifying a boundary on an intra-vascular ultrasound (IVUS) image, comprising:
   a computing device adapted to be electrically connected to a data-gathering device and to acquire data representative of a first intra-vascular ultrasound (IVUS) image and data representative of a second IVUS image from the data-gathering device data, the computer device performing the steps of:
   using a plurality of control points on a first IVUS image to identify additional control points on a second IVUS image;
   using said additional control points to identify a boundary on said second IVUS image;
   adjusting said boundary in accordance with at least one factor, said at least one factor being selected from a group consisting of: frequency factor, control-point factor and boundary factor, where said control-point factor corresponds to the connectivity of adjacent ones of said additional control points and said boundary factor corresponds to the curvature of said boundary.

19. The method of claim 18, further comprising using at least a portion of first IVUS data to identify said plurality of control points, said first IVUS data corresponding to said first IVUS image.

20. The method of claim 18, wherein said step of using a plurality of control points on a first IVUS image to identify additional control points on a second IVUS image further comprises extrapolating said plurality of control points on said second IVUS image.

21. A system, comprising:
   a computing device adapted to be electrically connected to a data-gathering device and to acquire data representative of a first intra-vascular ultrasound (IVUS) image and data representative of a second IVUS image from the data-gathering device data, the computing device programmed to:
   use a plurality of control points on the first IVUS image to identify additional control points on the second IVUS image;
   use the additional control points to identify a boundary on the second IVUS image; and
   adjust the boundary on the second IVUS image in accordance with at least one factor selected from a group consisting of: a frequency factor, a control-point factor, and a boundary factor, where the control-point factor corresponds to the connectivity of adjacent ones of the additional control points and the boundary factor corresponds to the curvature of said boundary.

22. The system of claim 21, wherein the computing device is further programmed to use the plurality of control points on the first IVUS image to identify additional control points on the second IVUS image by extrapolating the plurality of control points on the second IVUS image.

\* \* \* \* \*